US006101650A

United States Patent [19]

Omdal et al.

[11] Patent Number: 6,101,650

[45] Date of Patent: Aug. 15, 2000

[54] RECESSED ARM BOARD

[76] Inventors: David G. Omdal, 7801 Brookstone Ct., Ellicott City, Md. 21043; Scott J. Savader, 12152 Bayhill Dr., Carmel, Ind. 46033

[21] Appl. No.: 09/321,203

[22] Filed: May 27, 1999

[51] Int. Cl.[7] .............................. A61G 13/12; A61F 5/37

[52] U.S. Cl. .................................. 5/623; 5/646; 128/878

[58] Field of Search ............................... 5/623, 621, 624, 5/646, 647, 648, 650, 503.1, 507.1; 128/878, 879, 882, 845, 846; 378/208, 209; 602/20–23

[56] References Cited

U.S. PATENT DOCUMENTS

| | | | |
|---|---|---|---|
| 2,910,259 | 10/1959 | Johnson | 5/646 |
| 3,114,527 | 12/1963 | Demarest . | |
| 3,629,581 | 12/1971 | Smith . | |
| 3,861,666 | 1/1975 | Nishiyama et al. . | |
| 3,967,128 | 6/1976 | Smulewicz . | |
| 4,210,317 | 7/1980 | Spann et al. . | |
| 4,674,110 | 6/1987 | Eaton et al. | 5/647 |
| 4,681,308 | 7/1987 | Rice . | |
| 4,730,801 | 3/1988 | Cloward . | |
| 5,228,457 | 7/1993 | Kawamura | 5/647 |
| 5,537,702 | 7/1996 | Brown-Milants et al. | 5/632 |
| 5,549,121 | 8/1996 | Vinci | 128/878 |
| 5,657,369 | 8/1997 | Stein et al. | 378/209 |
| 5,742,962 | 4/1998 | Yoshino et al. | 5/623 |
| 5,785,057 | 7/1998 | Fischer | 128/878 |

*Primary Examiner*—Alexander Grosz
*Attorney, Agent, or Firm*—Nixon & Vanderhye

[57] ABSTRACT

An arm board is provided for supporting the arm during a surgical or imaging procedure in a manner that reduces the stress on the nerves and positions the arm in a more natural position for patient comfort, without interfering with the conduct of the surgical or imaging procedure. The arm board includes a main panel for being received under the patient and/or under a pad on the surgical table, and a trough portion for receiving and supporting the patient's forearm just below the height of the surgical table.

18 Claims, 3 Drawing Sheets

RECESSED ARM BOARD

FIELD OF THE INVENTION

The present invention relates to an accessory to for positioning a patient's limb during surgical and/or X-ray procedures and, more particularly, to an arm board for supporting the patient's arm below the plane of the body to permit a fluoroscopic procedure or other medical examination or procedure without interference from the arm.

BACKGROUND AND SUMMARY OF THE INVENTION

Percutaneous transhepatic cholangiogram and biliary drainage (PTCB) is procedure performed by an interventional radiologist, a medical doctor having specialty training in diagnostic radiology and subspecialty training in interventional radiology. This procedure involves placement of a needle followed by a wire and a catheter through the skin of the right flank after local anesthesia and sedation have been administered. This procedure is performed using sterile technique in a catherization laboratory in a hospital, using C-arm fluoroscopic (X-ray) guidance. The procedure allows the physician to look at the bile ducts and to bypass any obstructions of flow (biliary drainage) of bile from the liver into the small bowel where bile aids in the digestion of fatty foods.

Percutaneous biliary drainage (PBD) is a well described intervention used both as a temporizing procedure and as definitive therapy in patients with obstructive jaundice. Because these are invasive procedures, however, complications can occur. Complications commonly associated with PBD include cholangitis (13%–47%), fever secondary to bacteremia (11.2%), sepsis (3.9%–8.0%), hemobilia (3.5%–9.6%), pancreatitis (0%–10%), biloma formation (1%–3%), bile hypersecretion with electrolyte imbalance (5%), and death (0.6%–5.6%).

A previously unreported complication of PBD, brachial plexus neuropathy, has occurred twice during our last 617 cases, for an overall rate of 0.32%. Moreover, a single case of brachial plexus neuropathy has recently occurred in a patient undergoing a right heart catheterization in our lab.

The details of our aforementioned cases are reported herein below.

Case 1: A 58 year old female with a small pancreatic carcinoma and a nondilated biliary system was admitted to the department for preoperative placement of a PBD catheter. The stent was to be used as an aid during surgical reconstruction. The patient was placed on the table in a supine position with her right hand under her head and right arm in an abducted position, leaving the right lateral flank exposed for procedural access. Despite innumerable passes with a 22 gauge Chiba (Cook, Bloomington, Ind.) needle the nondilated biliary tract could not be pacified. The procedure was terminated after a time of approximately two hours. Nine mg midazolam hydrochloride and 450 ug fentanyl citrate was utilized for conscious sedation during the case. She was returned on the following day for a second attempt. The patient was again positioned described with her right arm abducted. Conscious sedation utilizing two mg midazolam hydrochloride and 100 ug fentanyl citrate was administered during a successful intubation procedure of the biliary tract. An 8F4 Percuflex (Medi-tech, Watertown, Mass.) biliary drain was placed.

Later that evening, the patient reported numbness in her arm and hand with an inability to clench her fist or lift her arm off the bed. A neurology consult was objected which reported findings consistent with a brachial plexus neuropathy. A motor and sensory grading of 3⁄5 for flexion and 3⁄5 for abduction at the shoulder combined with a limited 30 degree range of motion was documented. Sensory loss over the thumb and dorso-lateral aspect of the forearm was also present. Physical therapy was initiated and the patient regained complete motor and sensory function over the ensuing eight weeks.

Case 2: A 33 year old male was admitted to the department for percutaneous decompression of the biliary tract following a laparoscopic cholecystectomy injury. The patient was placed in a supine position with his right hand under his head and right arm in an abducted position. A right PBD was performed which demonstrated transection of the right hepatic duct with free spillage of contrast material into the peritoneal cavity. An 8Fr Percuflex (Medi-tech) biliary drain was placed. A total of six mg of midazolam hydrochloride and 200 ug of fentanyl citrate were utilized for conscious sedation. The patient reported nothing unusual during or immediately after the procedure. After the patient returned to his room, he noted that he was unable to move his right shoulder, arm, and hand. A neurology consult was obtained which reported findings consistent with a pan-brachial plexus neuropathy. Within 24 hours, he was markedly improved with grade 3⁄5 motor function in his forearm and hand; however, his deltoid function (shoulder shrug) remained graded at 0⁄5. Physical therapy was initiated and the patient regained complete motor and sensory function over the ensuing 26 days.

Case 3: A 13 year old female with a history of Tetrology of Fallot, pulmonary atresia and dextrocardia required evaluation for multiple episodes of pneumonia. A 2-dimensional echocardiogram demonstrated a right atrial pressure of 60 mm Hg and a right ventricular pressure of 70 mmHg secondary to a ventricular septal defect. A cardiac catheterization was desired to further evaluate the status of her pulmonary atresia for planning of potential balloon angioplasty and/or stent placement. One of our interventionalists (ACV) was present to assist if percutaneous intervention was necessary. The patient was placed in a supine position with both arms extended above her head. General anesthesia was utilized under the direction of the Pediatric Anesthesia department because of the age of the patient and the possible lengthy catheterization time. A diagnostic study with hemodynamics was performed but the right pulmonary artery system could not be effectively evaluated and thus no intervention was performed. The procedure time was four hours and 45 minutes. The patient was uneventfully recovered and discharged to home with no post procedure complaints reported or documented.

The following day, the patient was returned by her parents to the emergency room with complaints that her left arm felt like it was "twitching and asleep". A neurology consult was ordered. Fasciculations of the left deltoid, pectoralis, biceps, triceps, brachioradialis, and extensor policis muscle groups were noted. Motor strength was 5/5 in all muscle groups but sensation to pin-prick was decreased in the thumb and third and fourth digits. The neurologic findings were consistent with a brachial plexus injury focused on the C6–C7 nerve roots. Conservative care was recommended. The patient experienced a complete recovery over the ensuing two weeks.

The common factor in all three cases is the patient positioning utilized during these procedures. Traditionally, during a percutaneous transhepatic cholangiogram and biliary drainage proceedure, the patient lies supine with their ipsilateral (same side) arm hyperabducted, i.e. elbow displaced outwardly away from the side of the body, with the arm held above the patient's head to expose the flank, so that it does not interfere with catherization or imaging. It has become evident that positioning the arm in this manner stresses the nerves which travel from the neck to the arm.

More particularly, the mechanism for these three uncommon injuries is apparently a combined result of the stress placed on the brachial plexus during extension and/or abduction of the patient's arm at the shoulder (which was most likely compounded by the natural rotation of the head to the contralateral side), the procedure time, and the inability of the patient to report the occurrence of symptoms during the case secondary to the effects of conscious sedation. The patient positioning described for these procedures, namely extension and abduction of the arm at the shoulder and contralateral rotation of the head, is essentially identical to what is termed the 'Adson's maneuver'. See, e.g., Adson et al., "Cervical ribs: a method of anterior approach for relief of symptoms by division of the scalenius anticus," *Ann Surg* 1927; 85:839. This diagnostic test is commonly used in the evaluation of the individuals with suspected thoracic outlet syndrome. This maneuver is designed to hyperaccentuate compression of the neurovascular bundle as it passes through the costoclavicular space. Two other narrow anatomic regions of the thoracic outlet, the interscalene triangle and subcoracoid space, may also be affected. Longley et al. "Color Doppler ultrasound of thoracic inlet syndrome." *Semin Intervent Radiol,* 1990; 7:230–235.

Although the positive predictive value of Adson's maneuver is variable, cadaveric studies have demonstrated that similar positional maneuvers can causes strain and elongation of the C5–T1 nerve roots. Selvaratnam et al. "Differential strain produced by the brachial plexus tension test on the C5 to T1 nerve roots." *Proceedings of the 6th Biennial Conference of Manipulative Therapists Association of Australia,* 1989. A number of anatomic structures including cervical ribs, anomalous first ribs, fibrous bands, and hypertrophied muscles can contribute to the localized trauma and are associated with compression of the neurovascular bundle. Pang et al. "Thoracic outlet syndrome." *Neurosurgery* 1988; 22:105–121; Pollak, "Thoracic outlet syndrome: diagnosis and treatment." Mount Kisco, N.Y.: *Futura,* 1986. In 95% of cases of thoracic outlet syndrome, neurologic rather than vascular compromise is responsible for patient presentation, thus indicating the relative vulnerability of the brachial plexus in comparison to the subclavian artery and vein. These three cases would indicate that under the right combination of circumstances, even individuals without a history of thoracic outlet syndrome can experience a significant brachial plexus injury during a prolonged Adson's maneuver.

In summary, brachial plexus injuries can occur during percutaneous procedures if the patient's (ipsilateral) arm is hyperabducted to expose the flank. The risk of injury is most likely increased with lengthy procedure times, but the rare occurrence of this complication does not allow for speculation on safe time limits for this patient position. The use of deep conscious sedation during many procedures such as PBD and vascular intervention, through typically utilized with the patient's best interest in mind with respect to pain control, can also contribute to the risk of injury if patients are unable to respond to the ongoing brachial plexus trauma which can occur during the procedure. The third case clearly indicates the patients under general anesthesia are also at risk if they are positioned with their arms extended and/or abducted for improved access to peripheral intravenous lines.

This complication has grave significance, and there is a real potential for its occurrence during any interventional procedure in which the upper extremity is abducted away from the operative field.

Accordingly, it is an object of the present invention to provide a device that supports the ipsilateral, i.e., same side, arm during a surgical or imaging procedure in a manner that reduces the stress on the nerves and positions the arm in a more natural position for patient comfort, without interfering with the surgical or imaging procedure. It is further object of the invention to provide an arm positioning device that is of simple construction that may be provided as an accessory to provide a simple solution for avoidance of this iatrogenic injury.

The foregoing objects have been realized by providing a unique arm board having a 'well' for receiving the patient's forearm. The arm board places the patient's arm in a more neutral position, with the forearm just below the height of the table, so as not to overlap with the standard right mid-axillary line approach to the liver during PBD. For standard angiographic procedures, the patient's arm and hand are again below table top level, as opposed to adjacent to the body. Having the patient's arm positioned as such, the risk of a brachial plexus injury is eliminated. Moreover, the arm board is compatible with the necessary physician and C-arm positioning commonly utilized during a right PBD, other nonvascular procedures requiring similar patient positioning, and angiography.

BRIEF DESCRIPTION OF THE DRAWINGS

These, as well as other objects and advantages of this invention, will be more completely understood and appreciated by careful study of the following more detailed description of a presently preferred exemplary embodiment of the invention taken in conjunction with the accompanying drawings, of which.

DETAILED DESCRIPTION OF THE INVENTION

Figure 1:
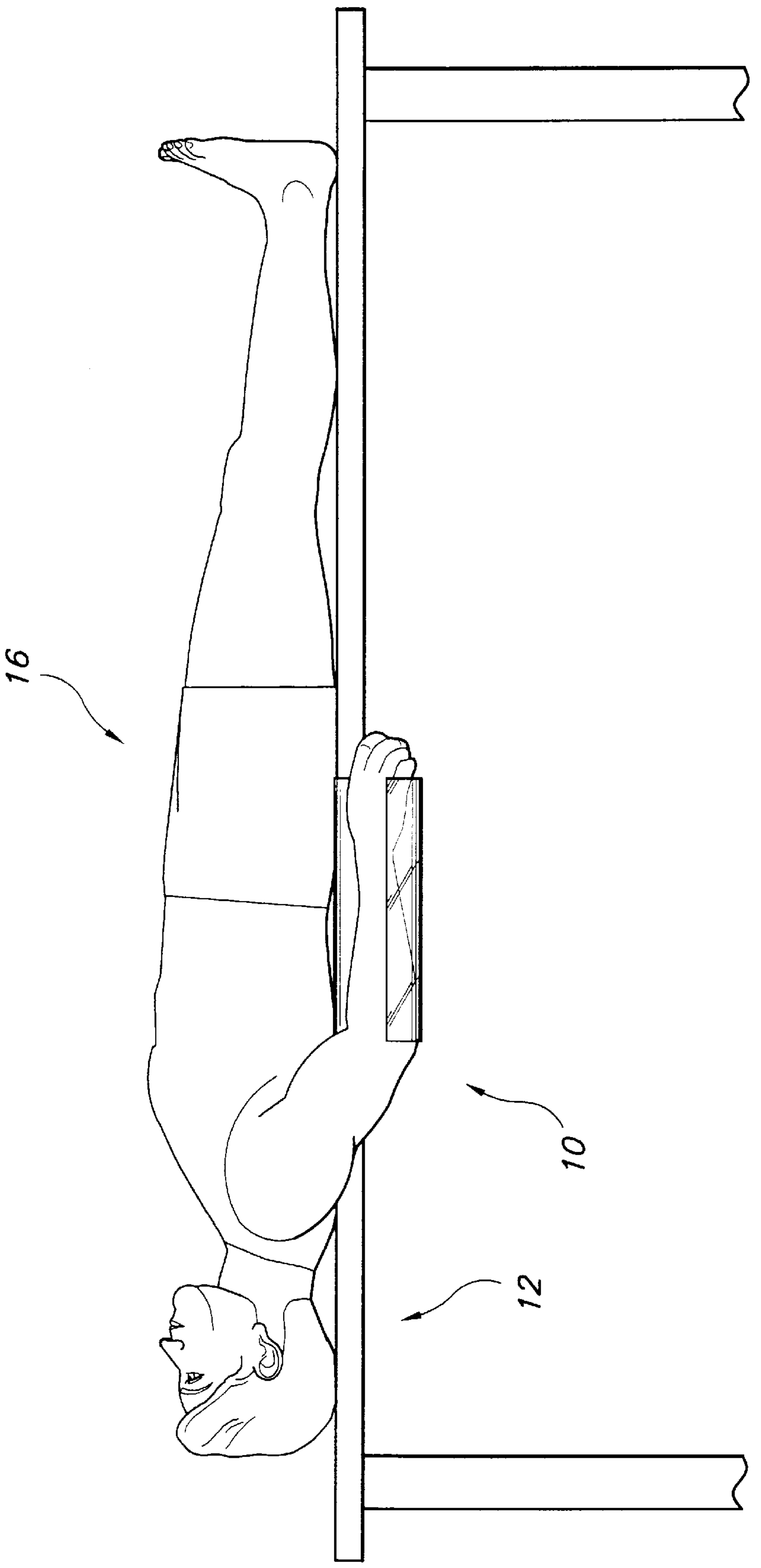
FIG. 1 is an elevational view of a patient lying on a supine position on a table with right arm disposed in a recessed arm board provided in accordance with the invention.
Figure 2:
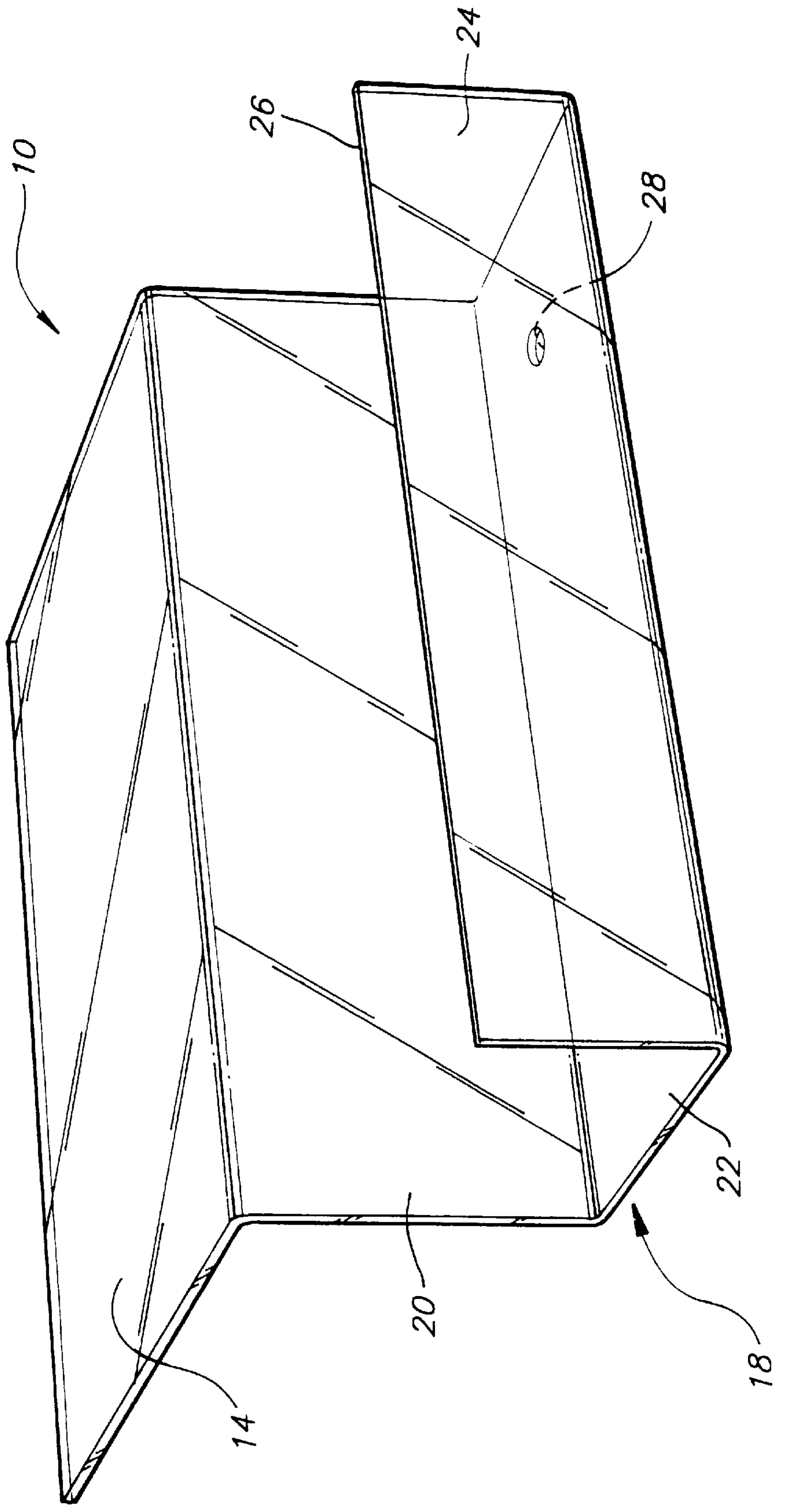
FIG. 2 is a perspective view of a recessed arm board provided in accordance with the presently preferred embodiment of the invention.
Figure 3:
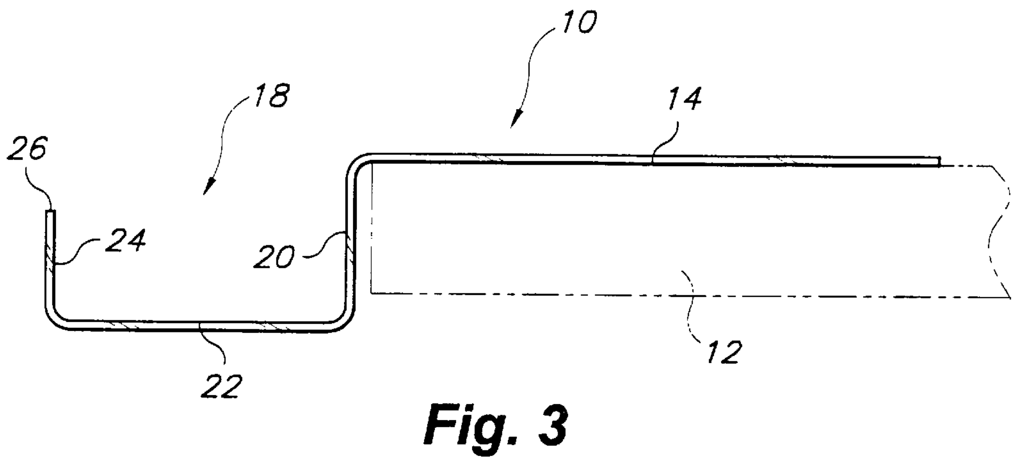
FIG. 3 is a side elevational view of the recessed arm board.
Figure 4:
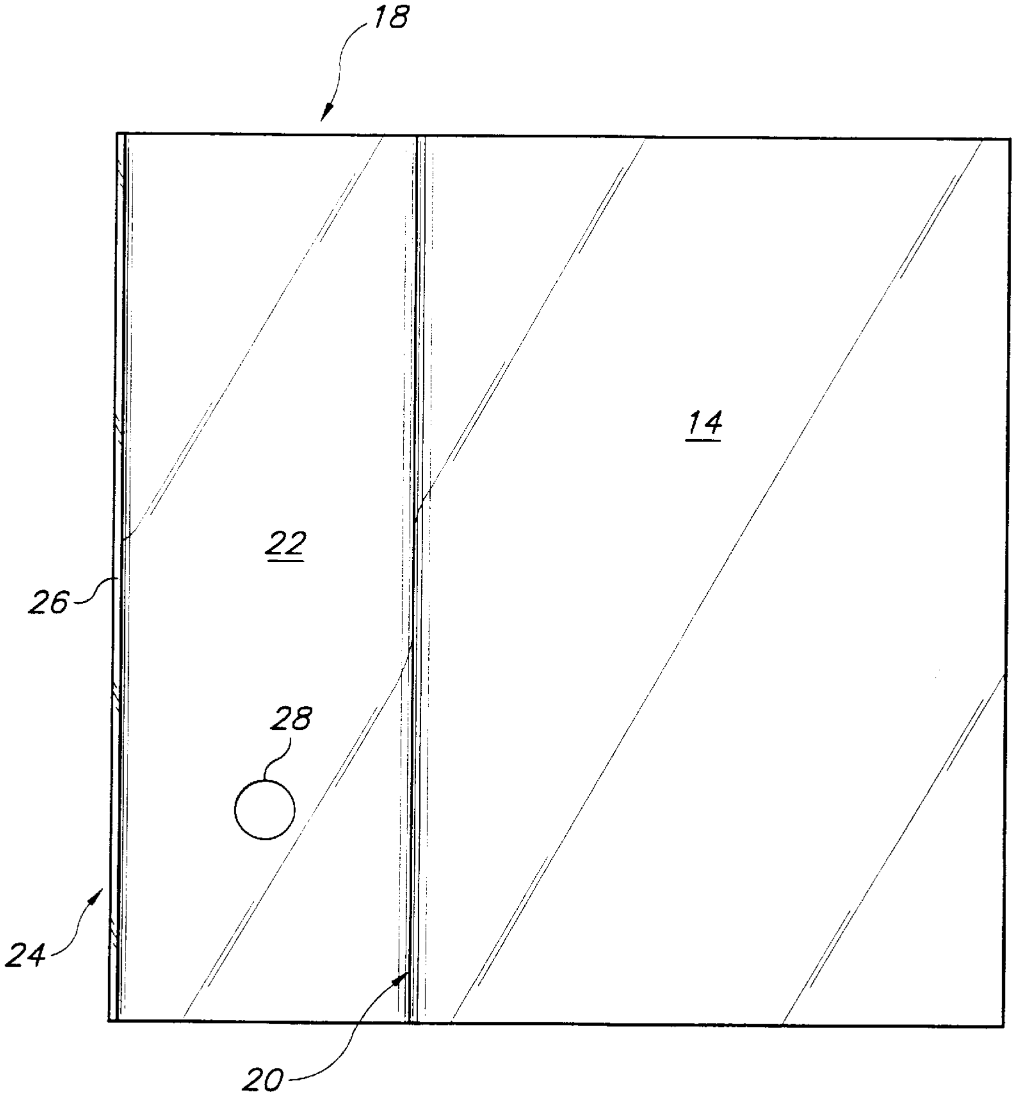
FIG. 4 is a top plan view thereof.

In accordance with the invention, a support 10 for the arm is provided that maintains the arm in a generally neutral, comfortable position that does not interfere with a catheterization or imaging procedure, does not project the arm out away from the patient (thus avoiding potential interference with movement of medical personnel around the fluoroscopic table), and minimizes stress on the nerves that travel from the neck to the ipsilateral arm.

Although the invention is described herein below with reference in particular to its use during a PTCB procedure, it is to be understood that the arm board 10 of the invention is adapted to and may be advantageously used in a variety of medical procedures including imaging procedures, examinations, and surgical procedures, in which it is necessary or desirable for the patient's arm(s) to be placed out of the plane of, to facilitate access to and viewing of, the torso.

Thus, in accordance with the invention, and by way of example, a recessed arm board 10 is provided that supports the ipsilaterial arm during a PTCB or PBD procedure, just below the height of fluoroscopic table 12 so as not to overlap with the standard right mid-axillary line approach to the liver. In contrast to prior arm positioning devices and techniques, the recessed arm board of the invention results in a change in position of the arm that greatly reduces the stress on the nerves which travel from the neck to the arm.

In the illustrated embodiment the recessed arm board is an accessory which is used when the arm is to be disposed out of the way during a catherization and/or imaging procedure. Thus, a first, horizontally extending main panel 14 of the arm board 10 is adapted to be disposed on the fluoroscopic table 12 under the patient's torso. As such, the main panel 14 has a width sufficient to extend from the edge of the fluoroscopic table 12, across at least a portion of the table that is to be occupied by the patient 16 to ensure that the patient's weight will hold the arm board 10 in position when the arm is resting on it and in a manner comfortable to the patient. As an alternative to disposing the horizontally extending main panel 14 of the arm board on the surface of the fluoroscopic table 12 immediately under the patient 16, a blanket, towel or other bedding (not shown) may be placed between the patient and the arm board main panel 14. Where the table has a thin pad or mattress, the main panel 14 may be placed thereunder.

As yet a further alternative (not illustrated) a specially adapted or modified table or like support structure may be provided that has a slotted side board for insertion of the horizontal main panel of the arm board. In that case, the arm board will not depend upon the patient's weight or other surface attachment structure for holding it in position. Those skilled in the art will appreciate that there are number of ways in which the placement of the arm board relative to the patient table or other support surface, and securement with respect thereto, can be established or augmented.

As noted above, the arm board of the invention is adapted to support the ipsolateral arm just below the height of the fluoroscopic table 12. Thus, the arm board of the invention provides a recessed portion or well 18 for receiving the patient's forearm. The forearm receiving recessed portion is defined by a first vertically extending panel 20 that extends downwardly from the main panel 14 and is adapted to be disposed in side-by-side parallel relation to the side board of the fluoroscopic table 12.

The recessed portion is further defined by a second horizontally extending support panel 22 that extends generally in parallel to the plane of the first, main panel 14 but is vertically offset therefrom by the first vertical panel 20.

Finally, to maintain the forearm in proper position in the recessed arm board a second vertical panel 24 is provided to define the maximum displacement of the forearm laterally from the patient's side. In the illustrated embodiment, the second vertical panel 24 has a height less than that of the first panel 20, as the second panel need only be high enough to retain the forearm in position but is desirably not so high as to obstruct access to the patient's arm, as may be desirable during the procedure, and/or interfere with placement of the patient's arm into or out of the recessed portion 18.

Although a variety of recessed arm board sizes could be provided, it is preferable that the recessed arm board be universally adapted to accommodate the forearm of any of a variety of patients. Thus, the height of the first and second vertical panels 20, 24 and the width of the support panel 22 are preferably selected so as to accommodate the dimensions of the most generously proportioned patient anticipated, to achieve the purpose of placing the patient's arm below the height of the fluoroscopic table. If necessary or desirable for patient comfort or proper arm placement, resilient pad(s) and/or blanket(s) or the like (not shown) may be placed in the trough 18 of the arm board and/or over the free edge 26 of the second vertical panel 24.

In accordance with a current adaptation, the recessed board has a length of about 30 cm and a width of about 30 cm so that overall, in plan view, the recessed arm board 10 is square. In this embodiment, the main, horizontal panel is about 20 cm wide whereas the trough 18 or forearm support panel 22 is about 10 cm wide. Finally, in the exemplary embodiment the trough 18 has a depth of, for example, between about 5 and 10 cm and more preferably between about 6 and 7 cm. In an exemplary embodiment the first vertical panel 20 may have a height of 9 or 10 cm and the second vertical panel 24 may have a height of about half to two thirds of that.

As presently proposed the recessed board is made from a radiolucent acrylic material, so as to ensure that there will be no interference with the fluoroscopic procedure.

With reference to the patient 16 shown in FIG. 1, it can be seen that the patient is place in a supine position on, for example, a fluoroscopic table 12 with the recessed arm board 10 positioning the same side arm slightly extended at the shoulder (elbow moves backwards in relation to the long axis of the body), e.g., about 15°, and slightly flexed, e.g., less than about 15°, at the elbow (forearm swings forward in relation to the long axis of the body). This is a near neutral position for the patient, minimizes the stress on the nerves running from the neck down the arm, and is a comfortable position for the patient which ensures that the patient will be relaxed and comfortable during the procedure. Moreover, this places the arm just below the height of the fluoroscopic table 12 so as not to overlap with the standard right mid-axillary line, (the line which bisects the body into a front and back half) approach to the liver during percutaneous biliary drainage.

As deemed necessary or desirable one or more apertures 28 may be provided through the support panel 22 at the base of the trough and/or through either or both of the vertical panels 20, 24 for the placement of wrist and/or forearm restraints, to ensure that the patient maintains his/her fore-arm in the proper non-obstructing position throughout the procedure in question.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An apparatus for positioning a patient's arm relative to a examining or operating table during a medical procedure, said apparatus comprising:

a first, main panel portion having a top surface and a bottom surface, a first longitudinal side edge, a second longitudinal side edge, a first end edge and a second end edge;

a trough portion for receiving a forearm of a patient, said trough portion including:

a first vertical panel having a first longitudinal side edge and a second longitudinal side edge, said first vertical panel extending generally downwardly from said first longitudinal side edge at said first longitudinal edge of said main panel;

a support panel extending generally horizontally from said second longitudinal edge of said first vertical panel, generally in parallel to but laterally offset from said main panel, from a first longitudinal side edge thereof at said second longitudinal side edge of said vertical panel to a second longitudinal side edge thereof; and a second vertical panel having a first longitudinal side edge and a second longitudinal side edge, said second vertical panel extending generally upwardly from said first longitudinal side edge thereof at said second longitudinal edge of said support panel, to said second longitudinal edge thereof, said second vertical panel having a height no greater than a height of said first vertical panel.

2. An apparatus as in claim 1, wherein a width of said main panel is at least about 2 times a width of said support panel.

3. An apparatus as in claim 1, wherein said main, vertical and support panels are formed of radiolucent acrylic material.

4. An apparatus as in claim 1, wherein a height of said second vertical panel is less than a height of said first vertical panel.

5. An apparatus as in claim 1, further comprising at least one aperture for receiving a securing or restraint strap defined in at least one of said vertical panels and said horizontal panel.

6. An apparatus as in claim 1, wherein said main panel is generally flat.

7. An apparatus as in claim 1, wherein said main panel, said vertical panels and said support panel are formed integrally as a one piece arm board.

8. A method for positioning a patient for a medical procedure, comprising:

providing a forearm positioner including:

a first, main panel portion having a top surface and a bottom surface, a first longitudinal side edge, a second longitudinal side edge, a first end edge and a second end edge; a trough portion for receiving a forearm of a patient, said trough portion including: a first vertical panel having a first longitudinal side edge and a second longitudinal side edge, said first vertical panel extending generally downwardly from said first longitudinal side edge at said first longitudinal edge of said main panel; a support panel extending generally horizontally from said second longitudinal edge of said first vertical panel, generally in parallel to but laterally offset from said main panel, from a first longitudinal side edge thereof at said second longitudinal side edge of said vertical panel to a second longitudinal side edge thereof; and a second vertical panel having a first longitudinal side edge and a second longitudinal side edge, said second vertical panel extending generally upwardly from said first longitudinal side edge thereof at said second longitudinal edge of said support panel, to said second longitudinal edge thereof, said second vertical panel having a height no greater than a height of said first vertical panel;

providing an examining or operating table having a support surface for receiving the patient during the medical procedure;

disposing the patient horizontally in a supine position on said table;

one of disposing said main panel on or operatively engaging said forearm positioner with said support surface so that said main panel is disposed vertically below the patient and the trough portion is generally aligned with the patient's forearm;

positioning the patient's forearm in said trough portion so that the patient's forearm is disposed generally just below the height of the support surface on which the patient is disposed; and initiating said medical procedure.

9. A method as in claim 8, wherein said step of providing a forearm positioner comprises providing a forearm positioner that has main, vertical and support panels formed of radiolucent acrylic material.

10. A method as in claim 9, wherein said panels are formed integrally in one piece.

11. An apparatus for a medical procedure comprising:

a patient table having a patient support surface disposed in a generally horizontal plane, a length extending along a first axis, and a width extending along a second axis generally perpendicular to the first axis;

an arm board including a first, main panel portion having a top surface and a bottom surface, a first longitudinal side edge, a second longitudinal side edge, a first end edge and a second end edge; and a trough portion for receiving a forearm of a patient, said trough portion including:

a first vertical panel having a first longitudinal side edge and a second longitudinal side edge, said first vertical panel extending generally downwardly from said first longitudinal side edge at said first longitudinal edge of said main panel;

a support panel extending generally horizontally from said second longitudinal edge of said first vertical panel, generally in parallel to but laterally offset from said main panel, from a first longitudinal side edge thereof at said second longitudinal side edge of said vertical panel to a second longitudinal side edge thereof; and a second vertical panel having a first longitudinal side edge and a second longitudinal side edge, said second vertical panel extending generally upwardly from said first longitudinal side edge thereof at said second longitudinal edge of said support panel, to said second longitudinal edge thereof, said second vertical panel having a height no greater than a height of said first vertical panel;

said main panel being one of disposed on said support surface or operatively engaged with said table so that said main panel is disposed on or vertically below the support surface and the trough portion of the arm board is disposed below the height of the table.

12. An apparatus as in claim 11, wherein a width of said main panel is at least about 2 times a width of said support panel.

13. An apparatus as in claim 11, wherein said main, vertical and support panels are formed of radiolucent acrylic material.

14. An apparatus as in claim 11, wherein a height of said second vertical panel is less than a height of said first vertical panel.

15. An apparatus as in claim 11, further comprising at least one aperture for receiving a securing or restraint strap defined in at least one of said vertical panels and said horizontal panel.

16. An apparatus as in claim 11, wherein said main panel is disposed on with said bottom surface thereof in parallel facing relation to a portion of the support surface of the table on which the patient is to be disposed.

17. An apparatus as in claim 11, wherein said main panel is generally flat.

18. An apparatus as in claim 11, wherein said main panel, said vertical panels and said support panel are formed integrally as a one piece arm board.

* * * * *